United States Patent [19]

Galardy et al.

[11] Patent Number: 5,270,326

[45] Date of Patent: * Dec. 14, 1993

[54] TREATMENT FOR TISSUE ULCERATION

[75] Inventors: Richard E. Galardy, Guilford, Conn.; Damian Grobelny, Surrey Hills, Australia; Gregory Schultz, Gainesville, Fla.

[73] Assignee: University of Florida, Gainesville, Fla.

[*] Notice: The portion of the term of this patent subsequent to Nov. 21, 2007 has been disclaimed.

[21] Appl. No.: 881,630

[22] Filed: May 12, 1992

Related U.S. Application Data

[63] Continuation of Ser. No. 616,021, Nov. 21, 1990, Pat. No. 5,114,953.

[51] Int. Cl.$^5$ .................. A61K 31/40; A61K 31/445
[52] U.S. Cl. .................. 514/323; 514/419; 514/563; 514/575; 514/925; 514/928
[58] Field of Search .............. 514/323, 419, 563, 575, 514/925, 928

[56] References Cited

U.S. PATENT DOCUMENTS 5,114,953 5/1992 Galardy et al. ............... 514/323

Primary Examiner—Leonard Schenkman
Attorney, Agent, or Firm—Morrison & Foerster

[57] ABSTRACT

Compounds of the formulas

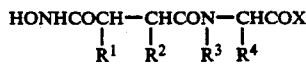

(1)

or

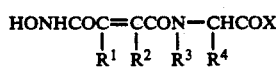 (2)

wherein
$R^1$ is H and $R^2$ is alkyl (3-8C) or wherein $R^1$ and $R^2$ taken together are $-(CH_2)_n-$ wherein $n=3-5$;
$R^3$ is H or alkyl (1-4C);
$R^4$ is a substituted or unsubstituted fused or conjugated bicycloaryl methylene;
X is $OR^5$ or $NHR^5$, wherein $R^5$ is H or substituted or unsubstituted alkyl (1-12C), aryl (6-12C), aryl alkyl (6-16C); or
X is an amino acid residue or amide thereof; or
X is the residue of a cyclic amine or heterocyclic amine
are useful for treating or preventing ulceration of tissue, especially cornea.

12 Claims, 2 Drawing Sheets

Days After Alkali Burn

TREATMENT FOR TISSUE ULCERATION

This invention was made with government support under National Institutes of Health grant R01 EY05587 and National Institutes of Health grant HL27368. The government has certain rights in the invention.

This application is a continuation of application Ser. No. 07/616,021 filed, Nov. 21, 1990, U.S. Pat. No. 5,114,953.

TECHNICAL FIELD

The invention is directed to pharmaceuticals which are useful in diseases characterized by unwanted collagenase activity. More specifically, the invention concerns hydroxamates which are dipeptide analogs that include fused or conjugated bicycloaryl substituents.

BACKGROUND ART

There are a number of enzymes which effect the breakdown of structural proteins and which are structurally related metalloproteinases. These include human skin fibroblast collagenase, human skin fibroblast gelatinase, human sputum collagenase and gelatinase, and human stromelysin. These are zinc-containing metalloproteinase enzymes, as are the angiotensin-converting enzymes and the enkephalinases.

Collagenase and related enzymes are important in mediating the symptomology of a number of diseases, including rheumatoid arthritis (Mullins, D. E., et al., *Biochim Biophys Acta* (1983) 695:117–214; the metastasis of tumor cells, (*ibid.*), Broadhurst, M. J., et al., EP application 276436 (1987), Reich, R., et al., *Cancer Res* (1988) 48:3307–3312); and various ulcerated conditions. Ulcerative conditions can result in the cornea as the result of alkali burns or as a result of infection by *Pseudomonas aeruginosa, Acanthamoeba, Herpes simplex* and vaccinia viruses. Other conditions characterized by unwanted matrix metalloprotease activity include periodontal disease and epidermolysis bullosa.

In view of the involvement of collagenase in a number of disease conditions, attempts have been made to prepare inhibitors to this enzyme. A number of such inhibitors are disclosed in EP applications 126,974 (published 1984) and 159,396 (published 1985) assigned to G. D. Searle. These inhibitors are secondary amines which contain oxo substituents at the 2-position in both substituents bonded to the amino nitrogen.

More closely related to the compounds of the present invention are those disclosed in U.S. Pat. Nos. 4,599,361 and 4,743,587, also assigned to G. D. Searle. These compounds are hydroxylamine dipeptide derivatives which contain, as one member of the dipeptide residue, a tyrosine or derivatized tyrosine residue or certain analogs thereof.

Tryptophan is also known to be therapeutic in various conditions, some of which may involve collagenase (see, for example, JP 57/058626; U.S. Pat. No. 4,698,342; 4,291,048). Also, inhibitors of bacterial collagenases have been disclosed in U.S. Pat. No. 4,558,034.

It has now been found that the compounds described below have superior inhibiting activity with respect to matrix metalloproteases. The invention compounds add to the repertoire of agents available for the treatment of conditions and diseases which are characterized by unwanted activity by the class of proteins which destroy structural proteins and designated "matrix metalloprotease" herein.

DISCLOSURE OF THE INVENTION

The invention provides new compounds which are useful to prevent or treat ulceration of tissue, especially corneal tissue. The compounds take advantage of the incorporation of tryptophan or other fused or conjugated bicycloaromatic amino acid residues in a hydroxylamate-derivatized dipeptide matrix metallo-protease inhibitor.

Accordingly, in one aspect, the invention is directed to treatment of ulcerated tissue with, and formulations for treating ulcerated tissue with, compounds of the formula:

or wherein
$R^1$ is H and $R^2$ is alkyl (3–8C) or wherein $R^1$ and $R^2$ taken together are —$(CH_2)_n$— wherein n=3–5;
$R^3$ is H or alkyl (1–4C);
$R^4$ is fused or conjugated unsubstituted or substituted bicycloaryl methylene;
X is $OR^5$ or $NHR^5$, wherein $R^5$ is H or substituted or unsubstituted alkyl (1–12C), aryl (6–12C), aryl alkyl (6–16C); or
X is an amino acid residue or amide thereof; or
X is the residue of a cyclic amine or heterocyclic amine.

MODES OF CARRYING OUT THE INVENTION

The invention compounds are inhibitors of mammalian matrix metalloproteases. As used herein, "mammalian matrix metalloprotease" means any enzyme found in mammalian sources which is capable of catalyzing the breakdown of collagen or gelatin under suitable assay conditions. Appropriate assay conditions can be found, for example, in U.S. Pat. No. 4,743,587 which references the procedure of Cawston, et al., *Anal Biochem* (1979) 99:340–345, use of a synthetic substrate is described by Weingarten, H., et al., *Biochem Biophys Res Comm* (1984) 139:1184–1187. Any standard method for analyzing the breakdown of these structural proteins can, of course, be used. The matrix metalloprotease enzymes referred to in the herein invention are all zinc-containing proteases which are similar in structure to, for example, human stromelysin or skin fibroblast collagenase.

The ability of candidate compounds to inhibit matrix metalloprotease activity can, of course, be tested in the assays described above. Isolated matrix metalloprotease enzymes can be used to confirm the inhibiting activity of the invention compounds, or crude extracts which contain the range of enzymes capable of tissue breakdown can be used.

The invention compounds can be considered modified dipeptides. At the "N-terminus" is the hydroxamate derivative of a succinic or maleic acid backbone, wherein the alternate carboxyl group forms the peptide bond with a "C-terminal" amino acid. The "C-terminal" amino acid is the residue of an amino acid which contains a fused or conjugated bicycloaromatic system, such as a tryptophan residue or a naphthylalanyl residue. The C-terminal residue can also be amidated or can be extended by one or two additional amino acid residues. Thus, the compounds of the invention can be prepared by reaction of the corresponding underivatized compounds which are carboxylic acids or esters of the maleic or succinic residue with hydroxylamine.

The "N-terminal" residue in formula 1 contains at least one and, in some instances, two chiral centers. Either configuration at either chiral center is included within the invention, as are mixtures of compounds containing the two possible configurations at each point of chirality. However, it is generally found that a particular configuration at each of these chiral centers is preferred. Similarly, in the compounds of formula 2, the double bond can be either the cis or trans configuration. In this case, also, one or the other configuration for a particular set of embodiments will be preferred. The carbon to which $R^4$ is bound is chiral in both formulas. While both configurations are included in the invention, that corresponding to an L-amino acid is preferred.

As used herein, "alkyl" has its conventional meaning as a straight chain, branched chain or cyclic saturated hydrocarbyl residue such as methyl, ethyl, isobutyl, cyclohexyl, t-butyl or the like. The alkyl substituents of the invention are of 1 to 12 carbons which may be substituted with 1 or 2 substituents. Substituents are generally those which do not interfere with the activity of the compound, including hydroxyl, "CBZ", amino, and the like. Aryl refers to aromatic ring systems such as phenyl, naphthyl, pyridyl, quinolyl, indolyl, and the like; aryl alkyl refers to aryl residues linked to the position indicated through an alkyl residue. "Acyl" refers to a substituent of the formula RCO— wherein R is alkyl as above-defined. "Cyclic amines" refer to those amines where the nitrogen is part of a heterocyclic ring, such as piperidine, "heterocyclic amines" refer to such heterocycles which contain an additional heteroatom, such as morpholine.

In the compounds of formula 1, preferred embodiments for $R^1$ and $R^2$ include those wherein $R^1$ is H and $R^2$ is isobutyl, 2-methyl butyl, or isopropyl. Especially preferred is isobutyl.

In both formula 1 and 2 compounds, preferred embodiments of $R^3$ are H and methyl, especially H.

$R^4$ is a fused or conjugated bicyclo aromatic system linked through a methylene group to the molecule. By "fused or conjugated bicyclo aromatic system" is meant a two-ringed system with aromatic character which may, further, contain one or more heteroatoms such as S, N, or O. When a heteroatom such as N is included, the system as it forms a part of formula (1) or (2), may contain an acyl protecting group (1–5C) attached to the nitrogen. Representative bicyclo fused aromatic systems include naphthyl, indolyl, quinolinyl, and isoquinolinyl. Representative conjugated systems include biphenyl, 4-phenylpyrimidyl, 3-phenylpyridyl and the like. In all cases, any available position of the fused or conjugated bicyclic system can be used for attachment through the methylene. The fused or conjugated aromatic system may further be substituted by 1–2 alkyl (1–4C) residues and/or hydroxy.

Preferred embodiments of $R^4$ include 1-(2-methyl naphthyl)methylene; 1-quinolyl methylene; 1-naphthyl methylene; 2-naphthyl methylene; 1-isoquinolyl methylene; 3-isoquinolyl methylene; 3-thionaphthenyl methylene; 3-cumaronyl methylene; 3-(5-methylindolyl)-methylene; 3-(5-hydroxyindolyl)methylene; 3-(2-hydroxyindolyl)methylene; biphenyl; and 4-phenylpyrimidyl.

Many of these substituents as part of an amino acid residue are described in Greenstein and Winitz, "Chemistry of the Amino Acids" (1961) 3:2731–2741 (John Wiley & Sons, N.Y.).

A particularly preferred embodiment of $R^4$ is 3-indolyl methylene or its N-acylated derivative—i.e., that embodiment wherein the "C-terminal" amino acid is a tryptophan residue or a protected form thereof. A preferred configuration at the carbon to which $R^4$ is bound is that corresponding to L-tryptophan.

Preferred embodiments of X are those of the formula $NHR^5$ wherein $R^5$ is H, substituted or unsubstituted alkyl (1–12C) or aryl alkyl (6–12C). Particularly preferred substitutions on $R^5$ are a hydroxyl group, or a phenylmethoxycarbamyl (CBZ) residue. In addition, the "dipeptide" may be extended by embodiments wherein X is an additional amino acid residue, particularly a glycyl residue, which may also be amidated as described.

Therapeutic Use of the Compound Inventions

As set forth in the Background section above, a number of diseases are known to be mediated by excess or undesired matrix-destroying metalloprotease activity. These include tumor metastasis, rheumatoid arthritis, ulcerations, particularly of the cornea, reaction to infection, and the like. The treatment of ulcerated tissue is effected by direct application of the compound or its composition if the tissue is accessible, or may require systemic administration if it is not.

The invention compounds can therefore be formulated into pharmaceutical compositions for use in treatment or prophylaxis of these conditions. Standard pharmaceutical formulation techniques are used, such as those disclosed in *Remington's Pharmaceutical Sciences*, Mack Publishing Company, Easton, Pa., latest edition. If the compounds are injected, they can be formulated for injection using excipients conventional for such purpose such as physiological saline, Hank's solution, Ringer's solution, and the like. Injection can be intravenous, intramuscular, intraperitoneal or subcutaneous. Dosage levels are of the order of 0.1 $\mu$g/kg of subject to 1 mg/kg of subject, depending, of course, on the nature of the ulceration, the nature of the subject, the particular embodiment of the invention compounds chosen, and the nature of the formulation and route of administration.

In addition to administration by injection, the compounds of the invention can also be formulated into compositions for transdermal or transmucosal delivery by including agents which effect penetration of these tissues, such as bile salts, fusidic acid derivatives, cholic acid, and the like. The invention compounds can also be used in liposome-based delivery systems and in formulations for topical and oral administration depending on the nature of the condition to be treated.

The inhibitors of the invention can be targeted to specific locations where the matrix metalloprotease is accumulated by using targeting ligands. For example, to focus the inhibitors to matrix metalloprotease contained in an ulcerated tissue, the inhibitor is conjugated to an antibody or fragment thereof which is immunoreactive with a tissue-specific marker as is generally understood in the preparation of immunotoxins in general. The targeting ligand can also be a ligand suitable for a receptor which is present on the tumor. Any targeting ligand which specifically reacts with a marker for the intended target tissue can be used. Methods for coupling the invention compound to the targeting ligand are well known and are similar to those described below for coupling to carrier. The conjugates are formulated and administered as described above.

For topical administration in directly treating ulcerated tissue, the compounds are formulated in a manner appropriate for the target tissue. For superficial ulcerations, the administration is generally in the form of salves, pastes, lotions, gels and the like. Typical excipients which are present in these formulations may be used to ease the application of the active ingredient to the diseased tissue.

When the ulcerated tissue is in the digestive tract, the compositions are formulated for oral administration using syrups, tablets, capsules, and the like. For less accessible lesions, sytemic administration as above described may be necessary.

Preparation and Use of Antibodies

The invention compounds can also be utilized in immunization protocols to obtain antisera immunospecific for the invention compounds. As the invention compounds are relatively small haptens, they are advantageously coupled to antigenically neutral carriers such as the conventionally used keyhole limpet hemocyanin (KLH) or serum albumin carriers. Coupling to carrier can be done by methods generally known in the art; the —COX functionality of the invention compounds offers a particularly convenient site for application of these techniques. For example, the COX residue can be reduced to an aldehyde and coupled to carrier through reaction with sidechain amino groups in protein-based carriers, optionally followed by reduction of imino linkage formed. The COX residue can also be reacted with sidechain amino groups using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill. Compounds 31–34 described in the examples below are designed to be coupled to antigenically neutral carriers through their C-terminal carboxyl groups (or amino groups in compound 32) using appropriate coupling agents.

The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures, now standard in the art, employing the invention compounds as antigens.

The antisera obtained can be used directly or monoclonal antibodies may be obtained by harvesting the peripheral blood lymphocytes or the spleen of the immunized animal and immortalizing the antibody-producing cells, followed by identifying the suitable antibody producers using standard immunoassay techniques.

The polyclonal or monoclonal preparations are then useful in monitoring therapy or prophylaxis regimens involving the compounds of the invention. Suitable samples such as those derived from blood, serum, urine, or saliva can be tested for the presence of the administered inhibitor at various times during the treatment protocol using standard immunoassay techniques which employ the antibody preparations of the invention.

The invention compounds can also be coupled to labels such as scintigraphic labels, e.g., technetium 99 or I-131, using standard coupling methods. The labeled compounds are administered to subjects to determine the locations of excess amounts of one or more matrix metalloproteases in vivo. The ability of the inhibitors to selectively bind matrix metalloprotease is thus taken advantage of to map the distribution of these enzymes in situ. The techniques can also, of course, be employed in histological procedures and the labeled invention compounds can be used in competitive immunoassays.

Use As Affinity Ligands

The invention compounds can be coupled to solid supports, such as separation membranes, chromatographic supports such as agarose, sepharose, polyacrylamide, and the like, or to microtiter plates to obtain affinity supports useful in purification of various mammalian matrix metalloproteases. The selective binding of the matrix metalloproteases to the inhibitor ligand permits the adsorption of the desired enzyme and its subsequent elution using, for example, altered ionic strength and/or pH conditions.

Preparation of the Invention Compounds

In general, the invention compounds are obtained by converting a carboxylic acid or ester precursor of the formulas or wherein R is H or alkyl (1–6C) to the corresponding hydroxamates by treating these compounds or their activated forms with hydroxylamine under conditions which effect the conversion.

In general, the hydroxylamine reagent is formed in situ by mixing the hydrochloride salt with an excess of KOH in methanol and removing the precipitated potassium chloride by filtration. The filtrate is then stirred with the precursor activated carboxylic acid or ester of formula 3 or 4 for several hours at room temperature, and the mixture is then evaporated to dryness under reduced pressure. The residue is acidified, then extracted with a suitable organic solvent such as ethyl acetate, the extract washed with aqueous potassium bisulfate and salt, and then dried with a solid drying agent such as anhydrous magnesium sulfate. The extract is then again evaporated to dryness and crystallized.

To prepare the starting materials of formulas 3 and 4, the monoesterified carboxylic acid of the formula

ROOCCHR$^1$CHR$^2$COOH or of the formula

ROOCCR$^1$CR$^2$COOH is reacted with the amino acid of the formula

NHR$^3$CHR$^4$COX wherein X is other than OH under conditions wherein the condensation to form the peptide bond occurs. Such conditions typically comprise mixture of the two components in a nonaqueous anhydrous polar aprotic solvent in the presence of base or a condensing agent such as a carbodiimide. Thus, the formation of the peptide linkage can be catalyzed in the presence of standard dehydration agents such as the carbodiimides, for example dicyclohexyl carbodiimide, or N, N-carbonyl diimidazole. The product is then recovered as a mixture of diastereomers of formula 3 or 4. This mixture is preferably used for the conversion to the hydroxamate as described above and one of the resulting diastereomers is crystallized directly from the product mixture. Alternatively, the diastereomers are separated by flash chromatography before conversion to the hydroxamate and recovered separately. This process is less preferred as compared to the process wherein separation of the diastereomers is reserved until the final product is obtained.

In the notation used in the examples, the "A" isomer is defined as that which migrates faster on TLC; the "B" isomer as that which migrates more slowly. When the "L" form of tryptophan or other amino acid containing a fused bicycloaromatic ring system is used as the "C-terminal" residue, in general, the "A" form is that which contains the corresponding configuration at the carbon containing the R$^2$ substituent (providing that is the only other center of asymmetry) in the final hydroxamate product. However, in Example 2, below, where D-tryptophan is included in the composition, the "B" isomer contains what would correspond to an "L" configuration at the carbon containing R$^2$ in the compounds of formula 1.

The components which form the compounds of formulas 3 and 4 are readily available in the case of tryptophan and its analogs as esters or amides.

As set forth above, many analogous fused bicyclo aromatic amino acids are described by Greenstein and Winitz (supra). Amino acids corresponding to those wherein R$^4$ is 1-(2-methyl naphthyl)methylene; 1-quinolyl-methylene; 1-naphthyl methylene; 1-isoquinolyl methylene; and 3-isoquinolyl methylene can be prepared from the bicyclo aromatic methylene halides using the acetamido malonic ester synthesis of amino acids, as is well understood in the art. The methylene halides themselves can be prepared from their corresponding carboxylic acids by reduction with lithium aluminum hydride and bromination of the resulting alcohol with thionyl bromide.

In some cases the derivatized maleic and succinic acid residues are also commercially available. If not, these can readily be prepared, in embodiments wherein R$^1$ is H by reaction of a 2-oxocarboxylic ester of the formula R$^2$COCOOR' in a Wittig reaction with an alkyl triphenylphosphoranylidene acetate. The methyl acetate is preferred, but any suitable ester can be employed. This reaction is conducted in a nonaqueous, nonpolar solvent usually at room temperature. The resultant compound is of the formula ROOCCR$^1$CR$^2$COOR', wherein R and R' are residues of esterifying alkyl or arylalkyl alcohols.

If the compounds of formula 4 are desired, this product is condensed with the appropriate tryptophan or analogous derivative; if the compounds of formula 3 are desired, the intermediate is reduced using hydrogen with a suitable catalyst. The sequence of reactions to obtain those embodiments wherein R$^1$ is H and R$^2$ is alkyl are shown in Reaction Scheme 1.

*The hydrogenation reaction will remove R' when R' = benzyl.

For those embodiments wherein R$^1$ and R$^2$ taken together are (CH$_2$)$_n$, the compounds of the invention are prepared analogously to the manner set forth in Reaction Scheme 1, except that the intermediate of the formula ROOCCHR$^1$CHR$^2$COOH is prepared from the corresponding 1,2-cycloalkane dicarboxylic acid—i.e., 1,2-cyclopentane dicarboxylic acid anhydride; 1,2-cyclohexane dicarboxylic anhydride or 1,2-cycloheptane dicarboxylic anhydride.

The following examples are intended to illustrate but not to limit the invention.

EXAMPLES

In the examples below, TLC solvent systems are as follows: (A) ethyl acetate/methanol (95:5); (B) ethyl acetate/methanol (25:5); (C) ethyl acetate; (D) ethyl acetate/methanol (30:5); (E) ethyl acetate/hexane (1:1); (F) chloroform/methanol/acetic acid (30:6:2).

EXAMPLE 1

Preparation of
N-[D,L-2-isobutyl-3-(N'-hydroxycarbonylamido)-propanoyl]-tryptophan methylamide A suspension of 5 g (0.033 mol) of the sodium salt of 4-methyl-2-oxopentanoic acid and 5.65 g (0.033 mol) of benzyl bromide in 10 ml of anhydrous dimethylformamide was stirred for 4 days at room temperature. After evaporation of the solvent under reduced pressure the residue was diluted to 100 ml with hexane and washed with water (3×20 ml) and saturated sodium chloride and dried over anhydrous magnesium sulfate. Evaporation of solvent gave 6.4 g (88% yield) of the benzyl ester of 4-methyl-2-oxopentanoic acid (1) as a colorless oil.

A mixture of 6.4 g (0.029 mol) of (1) and 9.7 g (0.029 mol) of methyl(triphenylphosphoranylidene)acetate in 100 mL of dry methylene chloride was stirred for 12 hr at room temperature and evaporated to dryness. The residue was extracted with hexane (3×50 mL). The hexane solution was washed with 10% sodium bicarbonate (2×30 mL), water and saturated sodium chloride and dried over anhydrous magnesium sulfate. Evaporation of the solvent gave 8.01 g (100% yield) of benzyl 2-isobutyl-3-(methoxycarbonyl)-propionate (2) as a mixture of E and Z isomers.

A mixture of 8.01 g (0.029 mol) of (2) and 1 g of 10% palladium on carbon in 50 mL of methanol was hydrogenated at room temperature under 4 atmospheres of hydrogen gas for 8 hr. After removal of the catalyst by filtration the filtrate was evaporated to dryness under reduced pressure to give 4.7 g (86% yield) of 2-isobutyl-3-(methoxycarbonyl)-propionic acid (3) as a colorless oil.

To a mixture of 0.85 g (4.5 mmol) of (3) and 0.57 g (4.5 mmol) of oxalyl chloride in 10 mL of dry methylene chloride 0.1 mL of anhydrous dimethylformamide was added. After stirring for 1 hr at room temperature the solvent was evaporated under reduced pressure and the residue was diluted to 5 mL with anhydrous dimethylformamide and 1.06 g (4.1 mmol) of the hydrochloride salt of L-tryptophan methylamide (Kortylewicz and Galardy, *J Med Chem* (1990) 33:263–273) was added followed by addition of 1.3 mL (9.3 mmol) of triethylamine at −10° C. This was stirred for 7 hr at room temperature and evaporated to dryness at room temperature under reduced pressure. The residue was diluted to 150 mL with ethyl acetate and washed with water (2×15 mL), 10% potassium bisulfate (5×20 mL), 10% sodium bicarbonate (2×20 mL), saturated sodium chloride and dried over anhydrous magnesium sulfate and then evaporated to give 1.6 g (83% yield) of N-[D,L-2-isobutyl-3-(methoxycarbonyl)-propanoyl]-L-tryptophan methylamide 4 as a mixture of diastereomers, 4A and 4B.

Isomers 4A and 4B were separated by flash chromatography (silica gel, ethyl acetate).

Isomer 4A: mp=134°–137° C. $R_f(C)=0.37$.
Isomer 4B: mp=156°–158° C. $R_f(C)=0.2$.

Alternatively, the mixture of 4A and 4B was converted directly to its hydroxamate as described below. In this case, 5A was crystallized from the mixture of 5A and 5B.

A warm mixture of 0.22 g (3.96 mmol) of potassium hydroxide in 1 mL of methanol was added to a warm mixture of 0.184 g (2.65 mmol) of the hydrochloride salt of hydroxylamine. After cooling in ice under an argon atmosphere the potassium chloride was filtered off and 0.5 g (1.32 mmol) of (4A) was added to the filtrate. The resulting mixture was stirred for 7 hr at room temperature and evaporated to dryness under reduced pressure. The residue was suspended in 100 mL of ethyl acetate and washed with 10 mL of 10% potassium bisulfate, saturated sodium chloride and dried over anhydrous magnesium sulfate and evaporated to dryness under reduced pressure. The residue was crystallized from ethyl acetate to give 0.28 g (56% yield) of pure 5A.

Isomer 4B was converted to its corresponding hydroxamic acid 5B (72% yield) as described for 4A.

Isomer 5A: mp=176°–182° C. $R_f(D)=0.45$.
Isomer 5B: mp=157°–162° C. $R_f(D)=0.39$.

For the case wherein the 4A/4B mixture is used, the 5A can be crystallized directly from the residue as described above.

In a similar manner to that set forth above, but substituting for 4-methyl-2-oxopentanoic acid, 2-oxopentanoic acid, 3-methyl-2-oxobutyric acid, 2-oxohexanoic acid, 5-methyl-2-oxohexanoic acid, or 2-decanoic acid, the corresponding compounds of formula 1 are prepared wherein $R^1$ is H and $R^2$ is an n-propyl, i-propyl, n-butyl, 2-methylbutyl, and n-octyl, respectively. In addition, following the procedures set forth hereinabove in Example 1, but omitting the step of hydrogenating the intermediate obtained by the Wittig reaction, the corresponding compounds of formula 2 wherein $R^1$ is H and $R^2$ is as set forth above are obtained.

To synthesize the compounds containing acylated forms of the indolyl residue, the intermediate ester of formula 3 or 4 is deesterified and acylated prior to conversion to the hydroxamate. For illustration, 4A is deesterified with sodium hydroxide in ethanol and then acidified to give N-(L-2-isobutyl-3-carboxypropanoyl)-L-tryptophan methylamide, which is treated with the anhydride of an alkyl (1-4C) carboxylic acid to obtain N-(L-2-isobutyl-3-carboxypropanoyl)-L-((N-acyl)indolyl)-tryptophan methylamide. This intermediate is then treated with oxalyl chloride followed by hydroxylamine at low temperature to give the corresponding hydroxamate.

EXAMPLE 2

Preparation of N-[2-isobutyl-3-(N'-hydroxycarbonylamido)-propanoyl]-D-tryptophan methylamide (7B)

The mixture of the two diastereoisomers of N-[2-isobutyl-3-(methoxycarbonyl)-propanoyl]-D-tryptophan methyl amide 6A,B was prepared as described for 4A,B in Example 1. The mixture was crystallized from ethyl acetate to give, after two recrystallizations, 0.26 g (49%) of the pure diastereomer 6B: mp 155°–157° C., $R_f(C)=0.32$. 6B was converted into its hydroxamic acid 7B by the method described in Example 1 in 50% yield (119 mg): mp 157°–159° C., $R_f(D)=0.39$.

EXAMPLE 3

Preparation of N-[2-isobutyl-3-(N'-hydroxycarbonylamido)-propanoyl]-N-methyl-L-tryptophan methylamide (9A)

The reaction of N-methyl-L-tryptophan-methylamide, prepared as described in Example 1 for L-tryptophan methylamide, with 3 performed as described for 4 gave crude N-[D,L-2-isobutyl-3-(methoxycarbonyl)-propanoyl]-N-methyl-L-tryptophan methylamide 8A,B which was crystallized from ethyl acetate to give 76 mg (19% yield) of 8A: mp 171°–174° C., $R_f(C)=0.40$.

8A was converted into 9A by the method described in Example 1 in 45% yield (34 mg): mp 180°–183° C., $R_f(D)=0.54$.

EXAMPLE 4

Preparation of N-[2-isobutyl-3-(N-hydroxycarbonylamido)-propanoyl]-L-3-(2-naphthyl)-alanine methylamide (11A)

N-[D,L-isobutyl-3-(methoxycarbonyl)-propanoyl]-L-3-(2-naphthyl)-alanine 10A was prepared as described in Example 1 from L-3-(2-naphthyl)-alanine methylamide and 3. The crude product was chromatographed on 60 g of silica gel in ethyl acetate:hexane 1:1 to yield 12 mg (5% yield) of 10A: mp 151°–158° C., $R_f(C)=0.69$.

10A was converted into the hydroxamate 11A as in Example 1 in 30% yield (3 mg): mp 179°–181° C., $R_f(D)=0.17$. MS-FAB (m/z) 400 (M+ +H).

EXAMPLE 5

Preparation of N-[2-isobutyl-3-(N'-hydroxycarbonylamido)-propanoyl]-L-tryptophan 2-hydroxyethylamide (13A)

The hydrochloride salt of L-tryptophan 2-hydroxyethylamide was prepared and coupled with 3 as described for the hydrochloride salt of L-tryptophan methylamide in Example 1 except that 3 was activated with 1,1'-carbonyldiimidazole for 20 minutes in methylene chloride at room temperature. The crude product was a mixture of 0.7 g (67% yield) of the diastereoisomers 12A,B: $R_f(C)$ 12A 0.38, $R_f(C)$ 12B 0.19.

12A crystallized from ethyl acetate in 35% yield (0.18 g): mp 161°–163° C., $R_f(C)=0.38$.

12A was converted into N-[2-isobutyl-3-(N'-hydroxycarbonylamido)-propanoyl]-L-tryptophan 2-hydroxyethylamide 13A as in Example 1 in 35% yield (62 mg): $R_f(D)=0.17$, mp 162°–163° C. MS-FAB (m/z) 419 (M+ +H).

EXAMPLE 6

Preparation of N-[2-isobutyl-3-(N'-hydroxycarbonylamido)-propanoyl]-L-tryptophan amylamide (15A)

The hydrochloride salt of L-tryptophan amylamide was prepared as described in Example 1 for L-tryptophan methylamide and was reacted with 3 that had been activated with 1,1'-carbonyldiimidazole for 20 minutes in dichloromethane at room temperature. The mixture of the two diastereomers of N-[D,L-2-isobutyl-3-(methoxycarbonyl)-propanoyl]-L-tryptophan amylamide 14A,B (90% yield) was converted to its corresponding hydroxamic acids as described for 4A. Slow evaporation of the ethylacetate solution gave 0.343 g (71%) of 15A,B: mp 160°–163° C. MS-FAB (m/z) 445 (M+ +H).

EXAMPLE 7

Preparation of N-[2-isobutyl-3-(N'-hydroxycarbonylamido)-propanoyl]-L-tryptophan piperidinamide (17A,B)

L-tryptophan piperidinamide was reacted with 3 as performed in Example 1 for L-tryptophan methylamide to give 1.14 g (89% yield) of N-[D,L-2-isobutyl-3-(methoxycarbonyl)-propanoyl]-L-tryptophan piperidinamide 16A,B as a foam; $R_f(C)$ (16A) 0.74, (16B) 0.67.

16A,B was converted into crude 17A,B identically to 4A in Example 1 in 88% yield (570 mg): $R_f(D)$ (17A) 0.41, (17B) 0.30. Crude 17A,B was chromatographed on 180 g of silica gel in 12% isopropanol in ethyl acetate to give 140 mg (25% yield) of 17A,B after crystallization from ethyl acetate: mp 169°–170° C. MS-FAB (m/z) 443 (M+ +H).

EXAMPLE 8

Preparation of N-[2-isobutyl-3-(N'-hydroxycarbonylamido)-propanoyl-L-tryptophan dodecylamide (19A)

The reaction of L-tryptophan dodecylamide was prepared in a manner analogous to that described for L-tryptophan methylamide in Example 1. This ester was reacted with 3 as described in Example 1 to give crude N-[D,L-isobutyl-3-(methoxycarbonyl)-propanol]-L-tryptophan dodecylamide 18A,B in 93% yield as a mixture of isomers 19A and 19B. This mixture was chromatographed on 150 g of silica gel in ethyl acetate:hexane, 1:2, to yield 0.62 g of the mixture of the two isomers: $R_f(E)$ 19A 0.37, $R_f(E)$ 19B 0.29.

Crystallization by slow evaporation from ethyl acetate gave 0.38 g of 18A contaminated by approximately 10% of 18B by TLC and NMR analysis: mp 133°–135° C. 18A was converted to its corresponding hydroxamic acid as described in Example 1, except that the potassium salt of 19A crystallized from the alkaline reaction mixture in 81% yield (222 mg). The potassium salt of 19A (54 mg) was dissolved in 2 mL of boiling methanol, a few drops of water were added, and the solution was acidified to pH 6 with 0.1N hydrochloric acid and diluted with water to give 50 mg (100% yield) of 19A: mp 155°–159° C., $R_f(D)=0.49$. MS-FAB (m/z) 543 (M+ +H).

EXAMPLE 9

Preparation of N-[2-isobutyl-3-(N'-hydroxycarbonylamido) propanoyl]-L-tryptophan (S)-methylbenzylamide (21A)

The reaction of L-tryptophan (S)-methylbenzylamide with 3 was performed as described in Example 1 to give, after crystallization from ethyl acetate, 330 mg (51% yield) of N-[2-isobutyl-3-(methoxycarbonyl)-propanoyl]-L-tryptophan (S)-methylbenzylamide 20A: mp 160°–162° C., $R_f(C)=0.77$.

20A was converted into hydroxamate 21A by the identical method used in Example 1 in 38% yield (76 mg): mp 165°–166° C., $R_f(D)=0.73$. MS-FAB (m/z) 479 (M+ +H).

EXAMPLE 10

Preparation of N-[L-2-isobutyl-3-(N'-hydroxycarbonylamido)-propanoyl]-L-tryptophan (6-phenylmethoxycarbonylamino-hexyl-1)amide (27A)

To prepare 1-amino-6-phenylmethoxycarbonylamino-hexane (23), an equimolar mixture (0.01 mol) of 1,6-diaminohexane and benzaldehyde in 25 mL of methylene chloride was stirred for 5 hr in the presence of 1.5 g of anhydrous magnesium sulfate at room temperature. After removing the drying agent by filtration the filtrate was evaporated to dryness under reduced pressure to give 2 g (100% yield) of crude 1-amino-6-phenylamino-hexane 22 as a colorless oil; NMR(CDCl$_3$) 1.1–1.9(m, 10H, hexane CH$_2$-2,-3,-4,-5, NH$_2$); 2.6(m, 2H, CH$_2$-1); 3.51(m, 2H, hexane CH$_2$-6); 7.1–7.8 (m, 5H, aromatic); 8.16(s, 1H, imine CH). To a mixture of 2 g (0.01 mol) of 22 and 1.4 mL (0.01 mol) of triethylamine in 20 mL of methylene chloride. Then 1.78 g (0.01 mol) of benzylchloroformate was added dropwise at −5° C. The resulting mixture was stirred for 0.5 hr at 0° C. and for 2 hr at room temperature then diluted to 50 mL with methylene chloride and washed with water (20 ml), 2% sodium bicarbonate (20 ml), water and saturated sodium chloride and dried over anhydrous magnesium sulfate. After evaporation of solvent under reduced pressure the residue was dissolved in 5 mL of ethanol and 10 mL of 2N hydrochloric acid was added. The resulting mixture was stirred for 6 hr at room temperature then evaporated to dryness under reduced pressure. The residue was diluted to 50 mL with water and washed with ethyl ether (2×15 ml). The water phase was evaporated under reduced pressure and the product 23 was purified by crystallization from a small portion of water with a yield of 42%; mp 175°-178° C.

To prepare the dipeptide analog (N-(L-2-isobutyl-3-methoxycarbonyl)-propanoyl-L-tryptophan (25A)), for derivatization to 23: To a mixture of 1.754 g (9.32 mmol) of 2-isobutyl-3-methoxycarbonylpropionic acid 3 in 4 mL of 50% anhydrous DMF in methylene chloride 1.66 g (10.2 mmol) of N,N'-carbonyldiimidazole (CDI) was added at room temperature. After 15 minutes of stirring at room temperature, 3.08 g (9.31 mmol) of the hydrochloride salt of L-tryptophan benzyl ester was added. The resulting mixture was stirred overnight at room temperature, then diluted to 60 mL with ethyl acetate and washed with 5% sodium bicarbonate (2×15 ml), water (2×15 ml), saturated sodium chloride solution and dried over magnesium sulfate. Evaporation of the solvent under reduced pressure gave 4.32 g (100% yield) of 24, the benzyl ester of 25 as a colorless foam, which was used in the next step without further purification.

Hydrogen gas was bubbled through a mixture of 4.32 g (9.31 mmol) of 24 and 0.5 g of 10% palladium on carbon in 15 mL of methanol for 2 hr while methanol was added to keep the volume of the reaction mixture constant. The catalyst was filtered off and washed with a fresh portion of methanol (15 ml) and the filtrate was evaporated to dryness under reduced pressure. Evaporation of the solvent under reduced pressure and drying of the residue in vacuo gave 3.08 g (88% yield) of acid 25A,B as a mixture of two diastereoisomers, in the form of a colorless glassy solid. This was separated to give isomers 25A and 25B by flash chromatography (silica gel; ethyl acetate; $R_f(25A)=0.24$, $R_f(25B)=0.1$).

The compound 25A was converted to N-[L-2-isobutyl-3-methoxycarbonylpropanoyl]-L-tryptophan (6-phenylmethoxycarbonylamino-hexyl-1)amide (26A) as follows. A mixture of 0.55 g (1.47 mmol) of 25A and 0.24 g (1.48 mmol) of CDI in 1 mL of 2% dimethylformamide in methylene chloride was stirred for 0.5 hr at room temperature and 0.42 g (1.47 mmol) of 23 was added. After stirring overnight at room temperature, the mixture was diluted to 50 mL with chloroform and washed with 2% potassium bisulfate (2×10 ml), water (10 ml), 5% sodium bicarbonate (2×10 ml), water (2×10 ml) and saturated sodium chloride and dried over anhydrous magnesium sulfate. Evaporation of the solvent under reduced pressure gave 0.8 g of the crude 26A which was purified by flash chromatography (silica gel; ethyl acetate/hexane 25:5): Yield 56%; $R_f(E)=0.57$.

When the product 26A is substituted for 4A in Example 1, the identical process afforded the title compound 27A, melting at 102°-108° C., in 46% yield; $R_f(D)=0.63$.

EXAMPLE 11

Preparation of
N-[L-2-isobutyl-3-(N'-hydroxycarbonylamido)-propanoyl]-L-tryptophan cyclohexylamide (28A)

When cyclohexylamine is substituted for 23 in Example 10, the identical process afforded the title compound 28A melting at 199°-203° C., in 49% yield; $R_f(D)=0.51$.

EXAMPLE 12

Preparation of N-[cis-2-(N'-hydroxycarbonylamido)-cyclohexylcarbonyl]-L-tryptophan methylamide (29A,B)

A mixture of 2 g (0.013 mol) of cis-1,2-cyclohexanedicarboxylic anhydride in 15 mL of methanol was refluxed for 5 hr, then evaporated to dryness under reduced pressure to give 2.41 g (100% yield) of cis-2-methoxycarbonyl-cyclohexanecarboxylic acid. When this was substituted for 3 in Example 1, the identical process afforded the title compound, melting at 140°-144° C., in 36% yield; $R_f(D)=0.53, 0.47$.

EXAMPLE 13

Preparation of
N-[trans-2-(N'-hydroxycarbonylamido)-cyclohexylcarbonyl]-L-tryptophan methylamide (30A,B)

When (±)trans-1,2-cyclohexanedicarboxylic anhydride was substituted for cis-1,2-cyclohexanedicarboxylic anhydride in Example 12, the identical process afforded the title compound 30A,B, melting at 167°-174° C., in 37% yield; $R_f(D)=0.57$.

EXAMPLE 14

Preparation of
N-[2-isobutyl-3-(N'-hydroxycarbonylamido)-propanoyl]-L-tryptophan (31A)

31A was prepared from 25A in Example 10 in a similar manner to the preparation of 5A in Example 1 in 75% yield (128 mg) and isolated as a foam from ethyl acetate: $R_f(F)=0.55$, MS-FAB (m/z) (M+ +H). A small sample of 31A recrystallized from ethyl acetate had a melting point of 116°-120° C.

EXAMPLE 15

Preparation of
N-(D,L-2-isobutyl-3-carboxypropanoyl)-L-tryptophan (6-aminohexyl-1)amide (32A)

A mixture of 0.5 g (8.24 mmol) of 26A in 0.4 mL of 2N potassium hydroxide in methanol was stirred overnight, then evaporated to dryness under reduced pressure. The residue was diluted to 15 mL with water and acidified to pH=2 with 1N hydrochloric acid. The crude free acid of 26A was taken up with ethyl acetate (3×15 ml) and the organic phase was dried over anhydrous magnesium sulfate and evaporated to dryness to give 0.45 g (92% yield) of 26A as a colorless foam.

Hydrogen gas was bubbled through a mixture of 0.395 g (6.6 mmol) of the free acid of 26A in 15 mL of methanol for 2 hr, in the presence of 0.12 g of 10% palladium on carbon at room temperature. The catalyst was filtered off, washed with ethanol (2×20 ml) and the filtrate was evaporated to dryness under reduced pressure to give 0.3 g (92% yield) of the title compound 32A as a colorless foam; $R_f(G)=0.08$.

EXAMPLE 16

Preparation of
N-[N-(2-isobutyl-3-carboxypropanoyl)-L-Tryptophanyl] glycine 34A,B The reaction of L-tryptophanyl-glycine methyl ester with acid 3, performed as described for 25A gave crude N-[N-(D,L-2-isobutyl-3-methoxycarbonylpropanoyl)-L-tryptophanyl]-glycine methyl ester 33 in 87% yield as a mixture of diastereomers 33A and 33B. Isomers 33A and 33B were separated by flash chromatography (silica gel; ethyl acetate). Isomer 33A mp=154°-155° C.; $R_f(C)=0.46$.

Esters 33A,B were transformed to free acids 34A,B by saponification with two equivalent of methanolic potassium hydroxide, as described for 25A. Isomer 34A yield 92%; mp=96°-102° C.; $R_f(G)=0.31$.

Isomer 34B yield 93%; mp=99°-105° C.; $R_f(G)=0.25$.

EXAMPLE 17

Preparation of
N-(cis-2-carboxy-cyclohexylcarbonyl)-L-tryptophan methylamide 35

To a mixture of 0.281 g (1.82 mmol) of cis-1,2-cyclohexanedicarboxylic anhydride and 0.47 g of the hydrochloride salt of L-Trp-NHMe in 0.5 mL of dimethylformamide 0.51 mL of triethylamine was added at room temperature. After 2 hr of stirring the resulting mixture was diluted to 10 mL with water and 25 mL of ethyl acetate was added. The resulting mixture was acidified to pH=2 with 10% potassium bisulfate and the organic phase was washed with water (2×15 ml), saturated sodium chloride and dried over anhydrous magnesium sulfate and evaporated to dryness. The title compound 35 was purified by crystallization from an ethyl acetate-hexane mixture. Yield 48%; mp=105°-112° C.; $R_f(G)=0.65, 0.61$.

EXAMPLE 18

Preparation of
N-(trans-2-carboxy-cyclohexylcarbonyl)-L-tryptophan methylamide 36

When (±) trans-1,2-cyclohexanedicarboxylic anhydride is substituted for cis-1,2-cyclohexanedicarboxylic anhydride in Example 17, the identical process afforded the title compound 36 in 56% yield: mp=167°-174° C.; $R_f(G)=0.67, 0.61$.

EXAMPLE 19

Assay of Inhibition Activity

Inhibitors were assayed against crude or purified human skin fibroblast collagenase using the synthetic thiol ester substrate at pH 6.5 exactly as described by Kortylewicz & Galardy, *J Med Chem* (1990) 33 263-273. The collagenase concentration was 1-2 nM. The compounds of Examples 1-18 are tested for their ability to inhibit crude collagenase and gelatinase from human skin fibroblasts, crude collagenase and gelatinase from purulent human sputum, and human stromelysin in this assay. The results with respect to crude enzyme preparation are shown in Table 1. The Ki of 5A for purified human skin collagenase purified as described in Kortylewicz & Galardy (ibid.) is 0.4 nM.

TABLE 1

| No. |  | Compound | $K_i$(nM) |
|---|---|---|---|
| 1 | 5A | NHOHCOCH$_2$CH(i-Bu)CO—L—Trp—NHMe | 10 |
| 1 | 5B | NHOHCOCH$_2$CH(i-Bu)CO—L—Trp—NHMe | 150 |
| 2 | 7A | NHOHCOCH$_2$CH(i-Bu)CO—D—Trp—NHMe | 70,000 |
| 3 | 9A | NHOHCOCH$_2$CH(i-Bu)CO—L—N—MeTrp—NHMe | 500 |
| 4 | 11A | NHOHCOCH$_2$CH(i-Bu)CO—L—Ala(2-naphthyl)NHMe | 15 |
| 5 | 13A | NHOHCOCH$_2$CH(i-Bu)CO—L—Trp—NH(CH$_2$)$_2$OH | 20 |
| 6 | 15A | NHOHCOCH$_2$CH(i-Bu)CO—L—Trp—NH(CH$_2$)$_4$CH$_3$ | 30 |
| 7 | 17A, B | NHOHCOCH$_2$CH(i-Bu)CO—L—Trp-piperidine | 200 |
| 8 | 19A | NHOHCOCH$_2$CH(i-Bu)CO—L—Trp—NH(CH$_2$)$_{11}$CH$_3$ | 300 |
| 9 | 21A | NHOHCOCH$_2$CH(i-Bu)CO—L—Trp—NH(S)CHMePh | 3 |
| 10 | 27A | NHOHCOCH$_2$CH(i-Bu)CO—L—Trp—NH(CH$_2$)$_6$NH—CBZ | 13 |
| 11 | 28A | NHOHCOCH$_2$CH(i-Bu)CO—L—Trp—NHcyclohexyl | 50 |
| 12 | 29A, B |  cis-NHOHCO—[cyclohexyl]—CO—L—Trp—NHMe | >10,000 |
| 13 | 30A, B |  trans-NHOHCO—[cyclohexyl]—CO—L—Trp—NHMe | >10,000 |
| 14 | 31A | NHOH—COCH$_2$CH(i-Bu)CO—L—Trp—OH | 200 |
| 15 | 32A | HOOC—CH$_2$CH(i-Bu)CO—L—Trp—NH(CH$_2$)NH$_2$ | >10,000 |
| 16 | 34A | HOCO—CH$_2$CH(i-Bu)CO—L—Trp—Gly—OH | >10,000 |
|  | 34B | HOCO—CH$_2$CH(i-Bu)CO—L—Trp—Gly—OH | >10,000 |
| 17 | 35 |  cis-HOCO—[cyclohexyl]—CO—L—Trp—NHMe | >10,000 |

TABLE 1-continued

| No. | Compound | K$_i$(nM) |
|-----|----------|-----------|
| 18  | 36  | >10,000 |

EXAMPLE 20
Prevention of Corneal Ulceration in the Alkali Burned Rabbit Cornea The ability of the invention compounds to prevent ulceration has been confirmed by a corneal assay conducted by Gregory Schultz, University of Florida, Gainesville, Fla.

Figure 1:
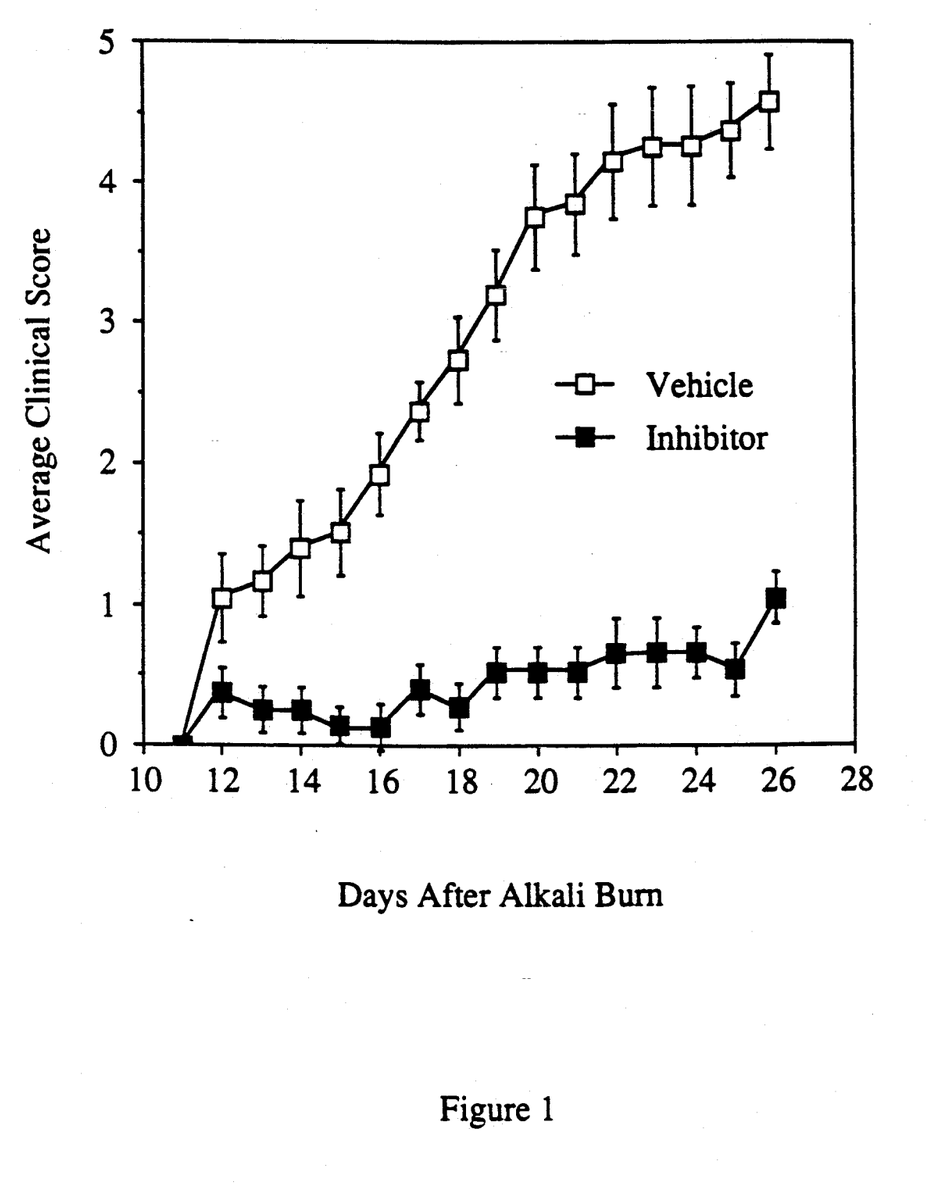
FIG. 1 is a graph which shows the effect of the inhibitor of the invention on corneal burns using a clinical scoring method.
Figure 2:
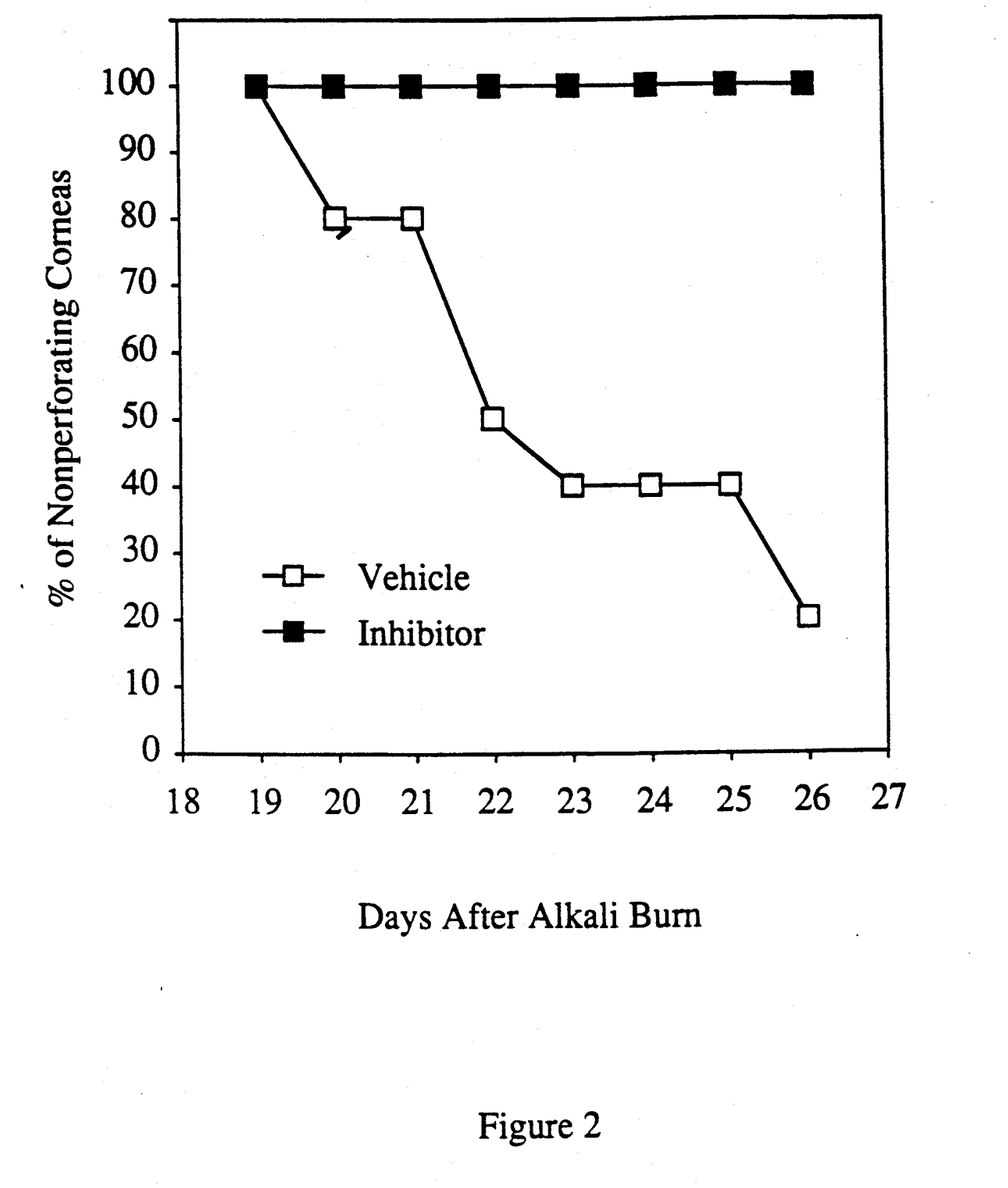
FIG. 2 shows the corresponding effect of the compound of the invention on corneal burns using a perforation criterion.

Twenty rabbit eyes were burned for 60 seconds with 1N NaOH to a diameter of 10 mm. The ten control eyes were treated with two drops of hypotonic buffer every two hours from 8 AM to 6 PM, and then with a subconjunctival injection of 0.5 mL of buffer in the evening. The experimental eyes were treated identically but with 400 μg per mL inhibitor in buffer. Eyes were scored clinically with 0 being no ulceration and 5 equalling perforation of the cornea. FIG. 1 shows average clinical score over 26 days. The compound 5A shows marked protection of the cornea from perforation. FIG. 2 shows percent of corneas not perforated over 26 days; compound 5A shows 100% protection.

A histological examination of the treated and untreated corneas showed the following:

Perpendicular sections though the corneas of rabbits were examined 28 days following severe alkali injuries which were made by exposing the corneas of anesthesized rats to 2N sodium hydroxide for 60 seconds in a 12.5 mm diameter well. Following injury, rabbits were treated topically with 2 drops every other hour between 8 AM and 6 PM followed by a subconjunctival injection of 0.5 mL of collagenase inhibitor of formula 5A or vehicle (50 mM Hepes, Antibiotics).

The cornea of a rabbit treated with collagenase inhibitor shows lamellae that have begun to repopulate with keratocytes which have most likely migrated from the uninjured peripheral cornea and sclera. The stroma also contains some inflammatory cells presumably macrophages which have migrated into the injured cornea There is little evidence for disruption of the extracellular matrix of the stromal lamellae and there is no evidence of significant extracellular matrix destruction. The epithelium in this section has resurfaced the cornea, although the epithelium is tenuously attached as evidenced by the separation of the sections of the epithelium from the underlying stroma. There is no evidence of neovascularization of this part of the cornea. The endothelial surface has not regenerated and Descemet's membrane has separated from the stroma in a cloudy cornea which lacks persistent and complete epithelial regeneration and also lacks significant stromal ulceration.

Cornea treated only with vehicle shows a dominant appearance of extensive degradation of the stromal matrix and the presence of massive inflammatory cell infiltrates. These inflammatory cells most probably are macrophages and neutrophils. The stromal lamellae have digested in this section approximately two-thirds of the complete depth of the stroma, and in adjacent sections, erosion has occurred to Descemet's membrane. The stroma appears to have a frayed appearance at the edge where the inflammatory cell infiltration is most extensive. Fracture lines running through the stroma suggest a general weakening of the extracellular matrix. In this section of the cornea there is no evidence of neovascularization, epithelial cells, or endothelial cells. Fragments of endothelial cells are present on Descemet's membrane together with inflammatory cells in the anterior chamber fluid. Few if any keratocytes can be identified in the stroma. This microscopic section is generally consistent with the results of slit lamp microscopy which indicated that the cornea had extensive ulceration and peripheral neovascularization.

Overall, the histopathology of these two sections suggest that a major effect of the collagenase inhibitor in preventing ulceration is due to a reduction in the inflammatory cell filtration into the alkali injured cornea. Furthermore, this section suggests that repopulation of the stroma in the collagenase inhibitor treated corneas has begun and incomplete epithelial regeneration of a transient nature has begun on the epithelial surface with no regeneration of the endothelium.

What is claimed is:

1. A method to treat or prevent ulceration of tissue which method comprises administering to a subject in need of such treatment an effective amount of a compound which inhibits at least one mammalian matrix metalloprotease, said compound having a formula selected from the group consisting of
NHOHCOCH$_2$CH(i-Bu)CO—L—Trp—NHMe;
NHOHCOCH$_2$CH(i-Bu)CO—L—N—MeTrp—NHMe;
NHOHCOCH$_2$CH(i-Bu)CO—L—Ala(2-naphthyl)NHMe;
NHOHCOCH$_2$CH(i-Bu)CO—L—Trp—NH(CH$_2$)$_2$OH;
NHOHCOCH$_2$CH(i-Bu)CO—L—Trp—NH(CH$_2$)$_4$CH$_3$;
NHOHCOCH$_2$CH(i-Bu)CO—L—Trp—piperidine;
NHOHCOCH$_2$CH(i-Bu)CO—L—Trp—NH(CH$_2$)$_{11}$CH$_3$;
NHOHCOCH$_2$CH(i-Bu)CO—L—Trp—NH(S)CHMePh;
NHOHCOCH$_2$CH(i-Bu)CO—L—Trp—NH(CH$_2$)$_6$NH—CBZ;
NHOHCOCH$_2$CH(i-Bu)CO—L—Trp—NHcyclohexyl; and
NHOHCOCH$_2$CH(i-Bu)CO—L—Trp—OH
or pharmaceutical composition thereof effective to treat or prevent said ulceration.

2. The method of claim 1 wherein the ulceration is of the cornea.

3. A pharmaceutical composition effective in treating or preventing ulceration of tissue which composition comprises an effective amount of a compound which inhibits at least one mammalian matrix metalloprotease, said compound having a formula selected from the group consisting of
NHOHCOCH$_2$CH(i-Bu)CO—L—Trp—NHMe;
NHOHCOCH$_2$CH(i-Bu)CO—L—N—MeTrp—NHMe;
NHOHCOCH$_2$CH(i-Bu)CO—L—Ala(2-naphthyl)NHMe;
NHOHCOCH$_2$CH(i-Bu)CO—L—Trp—NH(CH$_2$)$_2$OH;
NHOHCOCH$_2$CH(i-Bu)CO—L—Trp—NH(CH$_2$)$_4$CH$_3$;
NHOHCOCH$_2$CH(i-Bu)CO—L—Trp—piperidine;
NHOHCOCH$_2$CH(i-Bu)CO—L—Trp—NH(CH$_2$)$_{11}$CH$_3$;
NHOHCOCH$_2$CH(i-Bu)CO—L—Trp—NH(S)CHMePh;
NHOHCOCH$_2$CH(i-Bu)CO—L—Trp—NH(CH$_2$)$_6$NH—CBZ;
NHOHCOCH$_2$CH(i-Bu)CO—L—Trp—NHcyclohexyl; and
NHOHCOCH$_2$CH(i-Bu)CO—L—Trp—OH
to treat or prevent ulceration of tissue in admixture with a pharmaceutically acceptable excipient.

4. The composition of claim 3 wherein the ulceration is of the cornea, and wherein said pharmaceutical composition is in the form of an eyedrop composition.

5. The method of claim 1 wherein said inhibitor has the formula selected from the group consisting of
NHOHCOCH$_2$CH(i-Bu)CO—L—Trp—NHMe;
NHOHCOCH$_2$CH(i-Bu)CO—L—Ala(2-naphthyl)NHMe;
NHOHCOCH$_2$CH(i-Bu)CO—L—Trp—NH(CH$_2$)$_2$OH;
NHOHCOCH$_2$CH(i-Bu)CO—L—Trp—NH(CH$_2$)$_4$CH$_3$;
NHOHCOCH$_2$CH(i-Bu)CO—L—Trp—NH(S)CHMePh;
NHOHCOCH$_2$CH(i-Bu)CO—L—Trp—NH(CH$_2$)$_6$NH—CBZ; and
NHOHCOCH$_2$CH(i-Bu)CO—L—Trp—NHcyclohexyl.

6. The method of claim 5 wherein said inhibitor has the formula
NHOHCOCH$_2$CH(i-Bu)CO—L—Trp—NHMe.

7. The composition of claim 3 wherein said inhibitor has the formula selected from the group consisting of
NHOHCOCH$_2$CH(i-Bu)CO—L—Trp—NHMe;
NHOHCOCH$_2$CH(i-Bu)CO—L—Ala(2-naphthyl)NHMe;
NHOHCOCH$_2$CH(i-Bu)CO—L—Trp—NH(CH$_2$)$_2$OH;
NHOHCOCH$_2$CH(i-Bu)CO—L—Trp—NH(CH$_2$)$_4$CH$_3$;
NHOHCOCH$_2$CH(i-Bu)CO—L—Trp—NH(S)CHMePh;
NHOHCOCH$_2$CH(i-Bu)CO—L—Trp—NH(CH$_2$)$_6$NH—CBZ; and
NHOHCOCH$_2$CH(i-Bu)CO—L—Trp—NHcyclohexyl.

8. The composition of claim 7 wherein said inhibitor has the formula
NHOHCOCH$_2$CH(i-Bu)CO—L—Trp—NHMe.

9. The method of claim 2 wherein said inhibitor has the formula selected from the group consisting of
NHOHCOCH$_2$CH(i-Bu)CO—L—Trp—NHMe;
NHOHCOCH$_2$CH(i-Bu)CO—L—Ala(2-naphthyl)NHMe;
NHOHCOCH$_2$CH(i-Bu)CO—L—Trp—NH(CH$_2$)$_2$OH;
NHOHCOCH$_2$CH(i-Bu)CO—L—Trp—NH(CH$_2$)$_4$CH$_3$;
NHOHCOCH$_2$CH(i-Bu)CO—L—Trp—NH(S)CHMePh;
NHOHCOCH$_2$CH(i-Bu)CO—L—Trp—NH(CH$_2$)$_6$NH—CBZ; and
NHOHCOCH$_2$CH(i-Bu)CO—L—Trp—NHcyclohexyl.

10. The method of claim 9 wherein said inhibitor has the formula
NHOHCOCH$_2$CH(i-Bu)CO—L—Trp—NHMe.

11. The composition of claim 4 wherein said inhibitor has the formula selected from the group consisting of
NHOHCOCH$_2$CH(i-Bu)CO—L—Trp—NHMe;
NHOHCOCH$_2$CH(i-Bu)CO—L—Ala(2-naphthyl)NHMe;
NHOHCOCH$_2$CH(i-Bu)CO—L—Trp—NH(CH$_2$)$_2$OH;
NHOHCOCH$_2$CH(i-Bu)CO—L—Trp—NH(CH$_2$)$_4$CH$_3$;
NHOHCOCH$_2$CH(i-Bu)CO—L—Trp—NH(S)CHMePh;
NHOHCOCH$_2$CH(i-Bu)CO—L—Trp—NH(CH$_2$)$_6$NH—CBZ; and
NHOHCOCH$_2$CH(i-Bu)CO—L—Trp—NHcyclohexyl.

12. The composition of claim 11 wherein said inhibitor has the formula
NHOHCOCH$_2$CH(i-Bu)CO—L—Trp—NHMe.

* * * * *

UNITED STATES PATENT AND TRADEMARK OFFICE
CERTIFICATE OF CORRECTION

PATENT NO. : 5,270,326
DATED : December 14, 1993
INVENTOR(S) : Richard E. Galardy
Damian Grobelny
Gregory Schultz It is certified that error appears in the above-indentified patent and that said Letters Patent is hereby corrected as shown below:

"The portion of the term of this patent subsequent to Nov. 21, 2007 has been disclaimed." should read -- The portion of the term of this patent subsequent to May 19, 2009 has been disclaimed.--

Signed and Sealed this

Twenty-sixth Day of November 1996

Attest:

BRUCE LEHMAN

*Attesting Officer*   *Commissioner of Patents and Trademarks*